United States Patent
Yuba (10) Patent No.: US 10,478,093 B2
(45) Date of Patent: Nov. 19, 2019

(54) EXHALED-AIR PRESSURE MEASURING DEVICE

(71) Applicant: YUBA CORPORATION, Hiroshima (JP)

(72) Inventor: Tasuku Yuba, Hiroshima (JP)

(73) Assignee: YUBA CORPORATION, Hiroshima (JP)

( * ) Notice: Subject to any disclaimer, the term of this patent is extended or adjusted under 35 U.S.C. 154(b) by 0 days.

(21) Appl. No.: 16/109,212

(22) Filed: Aug. 22, 2018

(65) Prior Publication Data
US 2019/0069805 A1    Mar. 7, 2019

(30) Foreign Application Priority Data
Aug. 23, 2017   (JP) ................. 2017-159959

(51) Int. Cl.
*A61B 5/087*  (2006.01)
*A61B 5/08*   (2006.01)
*G01N 33/497* (2006.01)

(52) U.S. Cl.
CPC ............ *A61B 5/0803* (2013.01); *A61B 5/087* (2013.01); *G01N 33/497* (2013.01)

(58) Field of Classification Search
CPC ......... A61B 5/0803; A61B 5/087; A61B 5/08; A61B 5/071; A61B 5/0873; G01N 33/497
USPC ................................. 600/529–543
See application file for complete search history.

(56) References Cited

U.S. PATENT DOCUMENTS

| | | | | |
|---|---|---|---|---|
| 6,126,613 A | * | 10/2000 | Edwards | A61B 5/09 600/538 |
| 6,447,459 B1 | * | 9/2002 | Larom | A61B 5/0876 600/529 |
| 9,452,317 B2 | * | 9/2016 | Arkush | A61B 5/087 |

(Continued)

FOREIGN PATENT DOCUMENTS

| | | |
|---|---|---|
| JP | H08-164225 A | 6/1996 |
| JP | 3137944 U | 12/2007 |

(Continued)

OTHER PUBLICATIONS

Japanese Office Action dated Oct. 10, 2017 issued in corresponding Japanese Application No. JP 2017-159959.

*Primary Examiner* — Navin Natnithithadha
(74) *Attorney, Agent, or Firm* — Arent Fox LLP (57) ABSTRACT

To provide an exhaled-air pressure measuring device capable of deciding on exhaled-air pressure levels suitable for usage purposes. An exhaled-air pressure measuring device measures the pressure of air exhaled by a user, and on the basis of the measurement result, decides on an exhaled-air pressure level which corresponds to the pressure of the exhaled air. The exhaled-air pressure measuring device includes a measuring device body, and a mouthpiece portion from which the user exhales into the device. The measuring device body includes: a microcomputer which stores threshold data representing a threshold of the exhaled-air pressure level and decides on the exhaled-air pressure level corresponding to the exhaled-air pressure of a detection signal detected by a pressure sensor; and a USB terminal which is connected to an external storage device so as to change the threshold data stored in the microcomputer.

3 Claims, 4 Drawing Sheets (56) References Cited

U.S. PATENT DOCUMENTS

| | | | | |
|---|---|---|---|---|
| 2011/0009762 | A1* | 1/2011 | Eichler | A61B 5/085 600/532 |
| 2015/0011906 | A1* | 1/2015 | Wallach | A61K 36/00 600/538 |
| 2015/0258370 | A1* | 9/2015 | Arkush | A61B 5/087 482/8 |
| 2017/0071505 | A1* | 3/2017 | Stenzler | A61M 15/002 |
| 2017/0340213 | A1* | 11/2017 | Vespasiani | A61B 5/0205 |
| 2018/0008189 | A1* | 1/2018 | Wallach | A61K 36/00 |
| 2018/0140252 | A1* | 5/2018 | Luxon | A61B 5/03 |
| 2018/0318643 | A1* | 11/2018 | Klee | A61M 16/026 |

FOREIGN PATENT DOCUMENTS

| | | |
|---|---|---|
| JP | 2014-233471 A | 12/2014 |
| JP | 3194714 U | 12/2014 |
| JP | 2016-052375 A | 4/2016 |
| JP | 2016-112164 A1 | 4/2016 |
| JP | 6051479 B2 | 12/2016 |
| JP | 2017-035373 A | 2/2017 |

\* cited by examiner

EXHALED-AIR PRESSURE MEASURING DEVICE

CROSS-REFERENCE TO RELATED APPLICATION

This application claims priority to Japanese Patent Application No. JP 2017-159959, filed Aug. 23, 2017. The disclosure of the priority application is incorporated in its entirety herein by reference.

TECHNICAL FIELD

The present invention relates to an exhaled-air pressure measuring device which is capable of measuring the pressure of an exhaled air for the purposes of health promotion, medical treatment, training and the like.

Conventionally, a blowout has been mainly utilized as a toy for children, and a blowout utilizable for breathing exercises, for example, for the purposes of health promotion, medical treatment and the like, or as training, is also known (e.g., refer to Patent Document 1). This type of blowout includes a stretchable body (pouch-like portion) having a tube shape, and a wire spring arranged along the longitudinal directions of the stretchable body. If air is blown into the stretchable body from a blowing portion provided at an end thereof, then the stretchable body is stretched, while the stretchable body is curled into a spiral by the elastic force of the wire spring when air is not blown into it. In order to utilize the blowout repeatedly over a long period of time, the blowing portion is provided with a blowing-mouth cover formed of an antibacterial, flexible material, the blowing-mouth cover being attachable to and detachable from the blowing portion, so that the blowout can be kept hygienic even if it is repeatedly utilized over a long period of time.

The breathing exercises done using the blowout are given, for example, in the field of medicine, for the purpose of preventing infantile asthma, or to a patient with lung cancer, a patient who has a declining respiratory function under anesthesia before or after a surgical operation, a patient with a respiratory functional disorder such as a chronic obstructive pulmonary disease (COPD) caused by environmental pollution with PM 2.5 or the like, and the like. In the field of nursing care, the breathing exercises are given for the purpose of preventing an elderly person or a handicapped person from causing aspiration while eating, or as eating-deglutition rehabilitation for an elderly person or a handicapped person.

In the field of cosmetic treatment, it is given for the purpose of strengthening the cheek muscles of a person and thereby preventing a nasolabial sulcus from developing. In the field of music, a vocalist is able to train for how to breathe and how to vocalize, and in the field of sports, a person is able to heighten his/her blowing power in sports blowgun darts or the like as the training.

Some types of blowouts utilizable for various purposes as mentioned above are on the market, and those blowouts have a plurality of levels in the blowing force (required exhaling force) for stretching the stretchable body. For example, when a patient with a respiratory disease utilizes a blowout for treating the disease, the blowout needs to be suitable for the symptoms. Hence, an exhalation deciding device (e.g., refer to Patent Document 2) is known which is capable of quantitatively measuring a required exhaling force for a user, indicating an objective result of the measurement and making a decision easily on a blowout suitable for the required exhaling force for the user.

PRIOR ART DOCUMENTS

Patent Documents

[Patent Document 1] Registered Utility Model Publication No. 3137944
[Patent Document 2] Japanese Patent Publication No. 6051479

SUMMARY OF THE INVENTION

Problems to be Solved by the Invention

However, once a blowout suitable for the required exhaling force for a user is set by utilizing the exhalation deciding device, the blowout subjected to the setting could not be changed. For example, in the field of medicine, the exhalation deciding device is capable of deciding on a type of blowout suitable for symptoms of a user from among several types of blowouts. If the symptoms are improved, then again, it needs to decide on a blowout suitable for the improved symptoms. However, the required exhaling force can be greater than its range set in the exhalation deciding device. In that case, the exhalation deciding device is incapable of deciding on the suitable blowout, thereby requiring another exhalation deciding device. Besides, the exhalation deciding device is unavailable for purposes other than this usage.

Therefore, it is an object of the present invention to provide an exhaled-air pressure measuring device capable of deciding on exhaled-air pressure levels suitable for usage purposes.

Means for Solving the Problems

In order to solve the problems, an exhaled-air pressure measuring device in accordance with one aspect of the disclosure may include a mouthpiece portion to be held by a user in the mouth such that air is exhaled by the user; and a measuring device body which measures the pressure of the exhaled air into the mouthpiece portion by the user, and on the basis of a result of the measurement, decides on an exhaled-air pressure level which corresponds to the pressure of the exhaled air, wherein the measuring device body: includes a deciding section for deciding on the exhaled-air pressure level from the result of the measurement on the basis of a predetermined threshold of each of a plurality of the exhaled-air pressure levels; and is operable to change the threshold.

According to one aspect of the disclosure, in the disclosed exhaled-air pressure measuring device, the measuring device body is operable to change the threshold by acquiring threshold data which represents the threshold stored in an external storage device.

According to one aspect of the disclosure, in the disclosed exhaled-air pressure measuring device, the measuring device body is provided with a blowout including a stretchable body having a tube shape and changeable in shape, the stretchable body being stretched when air is exhaled into the blowout from the mouthpiece portion and being curled into a spiral when air is not exhaled into the blowout from the mouthpiece portion.

According to one aspect of the disclosure, in the disclosed exhaled-air pressure measuring device, the measuring device body includes an indication section indicating the exhaled-air pressure level.

Advantages of the Invention

In one aspect of the disclosure, the measuring device body of the exhaled-air pressure measuring device includes a deciding section for deciding on the exhaled-air pressure level from the result of the measurement on the basis of a predetermined threshold of each of a plurality of the exhaled-air pressure levels. Further, it is operable to change the threshold. Therefore, the threshold for deciding on the exhaled-air pressure level can be set to an exhaled-air pressure level suitable for a usage purpose.

In one aspect of the disclosure, the measuring device body is operable to change the threshold by acquiring threshold data stored in an external storage device. Therefore, the threshold for deciding on the exhaled-air pressure level can be easily set to an exhaled-air pressure level suitable for a usage purpose.

In one aspect of the disclosure, the measuring device body is provided with a blowout, and in measuring the pressure of exhaled air, the blowout is attached to the measuring device body. Therefore, a decision can be made on a blowout which has an exhaled-air pressure suitable for a usage purpose.

In one aspect of the disclosure, an indication section indicating the exhaled-air pressure level is provided, so that an objective decision can be made on an exhaled-air pressure level of a user.

MODE FOR CARRYING OUT THE INVENTION

An embodiment of the present invention will be below described with reference to the drawings.

Figure 1:
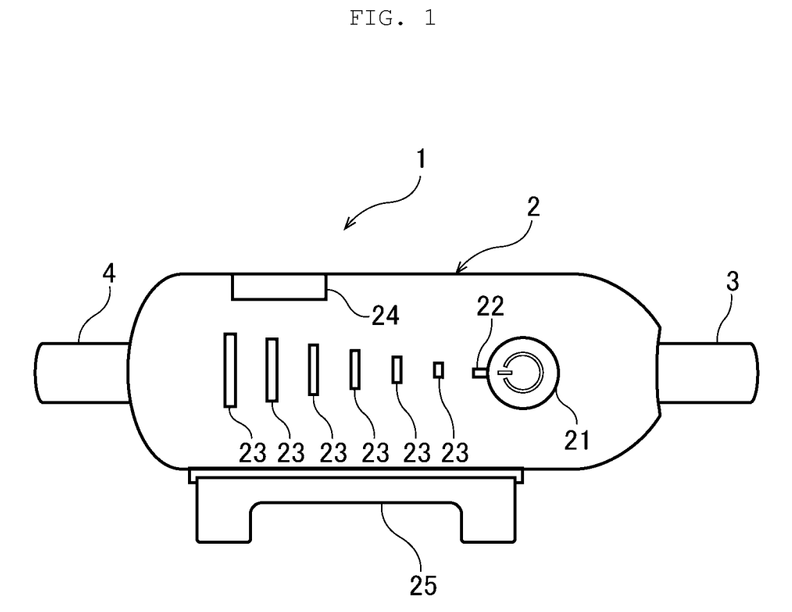
FIG. 1 is a schematic plan view of an exhaled-air pressure measuring device 1 according to an embodiment of the present invention.

FIGS. 1 to 4 show an exhaled-air pressure measuring device 1 according to the embodiment, and FIG. 1 is a schematic plan view of the exhaled-air pressure measuring device 1. The exhaled-air pressure measuring device 1 measures the pressure of air exhaled by a user, and on the basis of a result of the measurement, decides on an exhaled-air pressure level which corresponds to the pressure of the exhaled air. The exhaled-air pressure level is equivalent to a level obtained when dividing the exhaled-air pressure by a predetermined exhaled-air pressure value as the threshold. For example, there are seven levels: a level 0 indicating 0 $cmH_2O$-12 $cmH_2O$; a level 1, 12 $cmH_2O$-30 $cmH_2O$; a level 2, 30 $cmH_2O$-44 $cmH_2O$; a level 3, 44 $cmH_2O$-80 $cmH_2O$; a level 4, 80 $cmH_2O$-120 $cmH_2O$; a level 5, 120 $cmH_2O$-150 $cmH_2O$; and a level 6, 150 $cmH_2O$ or above. The exhaled-air pressure measuring device 1 mainly includes a measuring device body 2, a mouthpiece portion 3 and a blowout connection portion 4.

The measuring device body 2 is a main body of the exhaled-air pressure measuring device 1 and has a casing formed of a plastic resin or the like. The measuring device body 2 mainly includes a power switch 21, a power source LED 22, an exhaled-air-pressure level LED (indication section) 23, a USB terminal 24, and a blowout holder 25.

The power switch 21 is a switch for controlling the on/off of the electric power of the measuring device body 2, and the power switch 21 is pressed to switch the on/off. The light of the power source LED 22 is turned on when the electric power of the measuring device body 2 is turned on.

The exhaled-air-pressure level LED 23 is an LED for indicating, when a user exhales into the measuring device body 2, the pressure level of the exhaled air of the user. As shown in FIG. 1, for example, it is made up of six LEDs. In the exhaled-air-pressure level LED 23, for example, if the pressure level of the exhaled air is the level 1, then only the light of the LED at the right end in FIG. 1 is turned on. If the exhaled-air pressure level is the level 2, then the lights of the two LEDs from the right end are turned on. In the same manner, if it is the level 3, then the lights of the three LEDs from the right end are turned on: if it is the level 4, then the lights of the four LEDs from the right end are turned on: if it is the level 5, then the lights of the five LEDs from the right end are turned on: and if it is the level 6, then the lights of all the LEDs are turned on.

The USB terminal 24 is a terminal which connects with an external device, and the connection is made by inserting a USB connector therein. The USB terminal 24 is a terminal which connects with an external storage device (e.g., a PC or the like) for the purpose of changing threshold data stored in a microcomputer 27 (described later), or it is used for charging a power source unit 28. The blowout holder 25 is used for holding a blowout 6 (described later) when the blowout 6 is not utilized.

The mouthpiece portion 3 is a portion to be held by a user in the mouth such that air is exhaled by the user. The mouthpiece portion 3 is arranged in a cylinder shape on an end side of the measuring device body 2 and is formed of, for example, a plastic resin or the like. The mouthpiece portion 3 has, for example, a mouthpiece 7 (described later) attached thereto.

The blowout connection portion 4 is a portion to be connected to a mouthpiece body 61 of the blowout 6 (described later) when the blowout 6 is utilized. The blowout connection portion 4 is arranged in a cylinder shape on the other end side of the measuring device body 2 and is formed of, for example, a plastic resin or the like. For example, a blowout is utilized for breathing exercises, or training, and in accordance with the above exhaled-air pressure levels, there are several types of such blowouts which correspond to, for example, the level 1 to the level 3. A decision needs to be made whether a blowout is suitable for the exhaled-air pressure of a user. The blowout 6 is connected to the blowout connection portion 4, and then, the user exhales into the measuring device body 2. A decision is made whether the exhaled-air pressure level of the user has reached the exhaled-air pressure level of the blowout 6. Specifically, for example, the blowout 6 is set to the level 3 as the exhaled-air pressure level and is connected to the blowout connection portion 4. If the exhaled-air pressure level of a user has reached the level 3 when the user exhales, then the lights of the three LEDs 23 from the right end are turned on (the level 3). On the other hand, if the exhaled-air pressure level of the user has not reached the level 3, then the lights of the LEDs 23 corresponding to the level 0 to the level 2 are turned on in accordance with the exhaled-air pressure level of the user. For example, the blowout 6 is set to the level 1 as the exhaled-air pressure level and is connected to the blowout connection portion 4. If the exhaled-air pressure level of the user has reached the level 1 when the user exhales, then only the light of the LED 23 at the right end is turned on (the level 1). On the other hand, if the exhaled-air pressure level of the user has not reached the level 1, the lights of all the LEDs 23 remain turned off.

In addition, without utilizing the blowout 6, a decision can be made on the exhaled-air pressure level of a user. In the case, an attachment 5A (described later) is attached to the blowout connection portion 4. The user exhales into the measuring device body 2, and thereby, the lights of the LEDs which correspond to the level 0 to the level 7 are turned on in accordance with the exhaled-air pressure level of the user.

Figure 2:
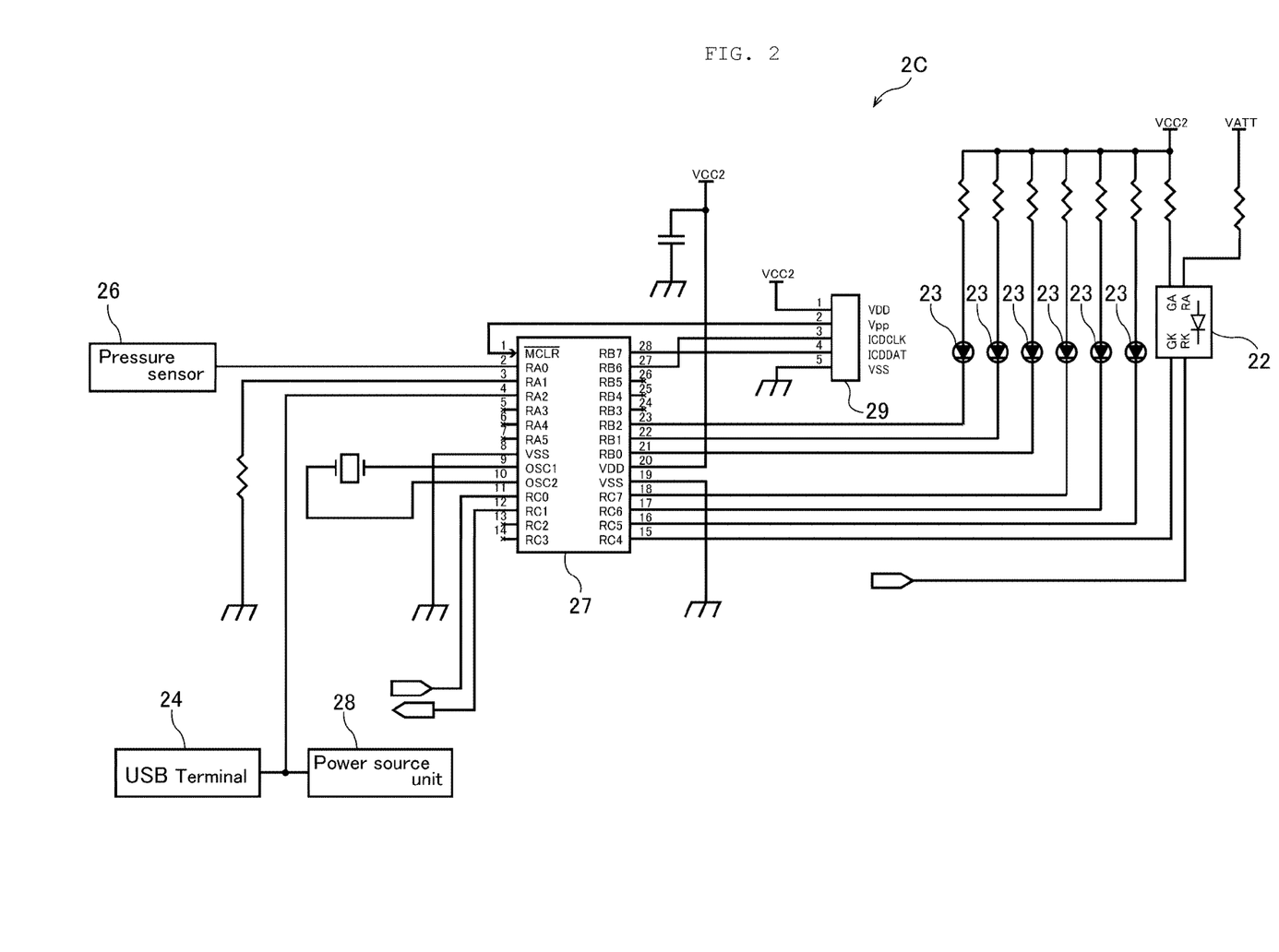
FIG. 2 is a circuit formation diagram showing an internal circuit 2C of a measuring device body 2 shown in FIG. 1.

FIG. 2 is a circuit formation diagram showing an internal circuit 2C of the measuring device body 2 of FIG. 1. This circuit is formed on an electronic circuit board arranged inside of the measuring device body 2. This circuit is formed by: the above power source LED 22, exhaled-air-pressure level LEDs 23 and USB terminal 24, a pressure sensor 26, the microcomputer (deciding section) 27, the power source unit 28, and an external connection terminal 29.

The pressure sensor 26 is a sensor which measures air pressure (the pressure of air exhaled by a user in the embodiment) and outputs a detection signal. The pressure sensor 26 is provided, for example, with an ICC-terminal, an N-sub-terminal, a GND-terminal, a Vout(+)-terminal and a Vout(−)-terminal. The ICC-terminal and the N-sub-terminal are each a power source terminal, and an output terminal of a constant-current circuit (e.g., an op-amp) supplying a constant electric current is connected thereto. The GND-terminal is a ground terminal and is grounded. The Vout(+)-terminal and the Vout(−)-terminal are each an output terminal and connected via an instrumented amp or the like to an input terminal of the microcomputer 27, so that a detection signal is outputted to the microcomputer 27.

The microcomputer 27 is a microchip which controls the entire measuring device body 2. It includes: a power source terminal RA2 which connects with the USB terminal 24 and the power source unit 28; an input terminal RA0 which connects with the pressure sensor 26; and output terminals RB0, RB1, RB2, RC4, RC5, RC6 and RC7 each of which connects with the power source LED 22 and the exhaled-air-pressure level LEDs 23 respectively. The power source terminal RA2 is supplied with electric power, and thereby, the microcomputer 27 turns on the light of the power source LED 22. The microcomputer 27 has the above thresholds of the level 0 to the level 7 stored therein; the threshold data indicating 12 cmH$_2$O, 30 cmH$_2$O, 44 cmH$_2$O, 80 cmH$_2$O, 120 cmH$_2$O and 150 cmH$_2$O. Upon receiving a detection signal from the pressure sensor 26, the microcomputer 27 decides whether the exhaled-air pressure of the detection signal is equivalent to any of the level 0 to the level 7.

Next, the microcomputer 27 turns off the lights of all the exhaled-air-pressure level LEDs 23 if the decision result is the level 0. If the decision result is the level 1, then it turns on the light of the one of the exhaled-air-pressure level LEDs 23 (the LED at the right end in FIG. 1). If the decision result is the level 2, then it turns on the light of the two of the exhaled-air-pressure level LEDs 23 (the two LEDs from the right end in FIG. 1). If the decision result is the level 3, then it turns on the light of the three of the exhaled-air-pressure level LEDs 23 (the three LEDs from the right end in FIG. 1). If the decision result is the level 4, then it turns on the light of the four of the exhaled-air-pressure level LEDs 23 (the four LEDs from the right end in FIG. 1). If the decision result is the level 5, then it turns on the light of the five of the exhaled-air-pressure level LEDs 23 (the five LEDs from the right end in FIG. 1). If the decision result is the level 6, then it turns on the light of all the exhaled-air-pressure level LEDs 23. The power source LED 22 and the exhaled-air-pressure level LEDs 23 are individually connected to the corresponding output terminals of the microcomputer 27, so that they can emit light when supplied with electric power through the control by the microcomputer 27.

The power source unit 28 is a battery which supplies the measuring device body 2 with electric power, and is formed, for example, by a rechargeable battery or the like. The power source unit 28 is connected to the USB terminal 24, and into the USB terminal 24, the USB connector is inserted, the USB connector being connected to an external device. The external device supplies electric power and begins charging the power source unit 28.

The external connection terminal 29 is connected to an external device so that software can be written in the microcomputer 27. It is utilized for the default setting or repair of the exhaled-air pressure measuring device 1.

The threshold data stored in the microcomputer 27 is changeable by connecting an external storage device to the USB terminal 24. Specifically, the external storage device operates to replace the threshold data with other data, thereby making the above threshold data changeable. For example, the above exhaled-air pressure levels are aimed at the usage of the exhaled-air pressure measuring device 1 in the field of medicine or nursing care. However, the exhaled-air pressure becomes higher when it is utilized in the field of cosmetic treatment or sports. Therefore, the threshold data are replaced with other data, so that the exhaled-air pressure measuring device 1 can be utilized for other purposes.

Figure 3:
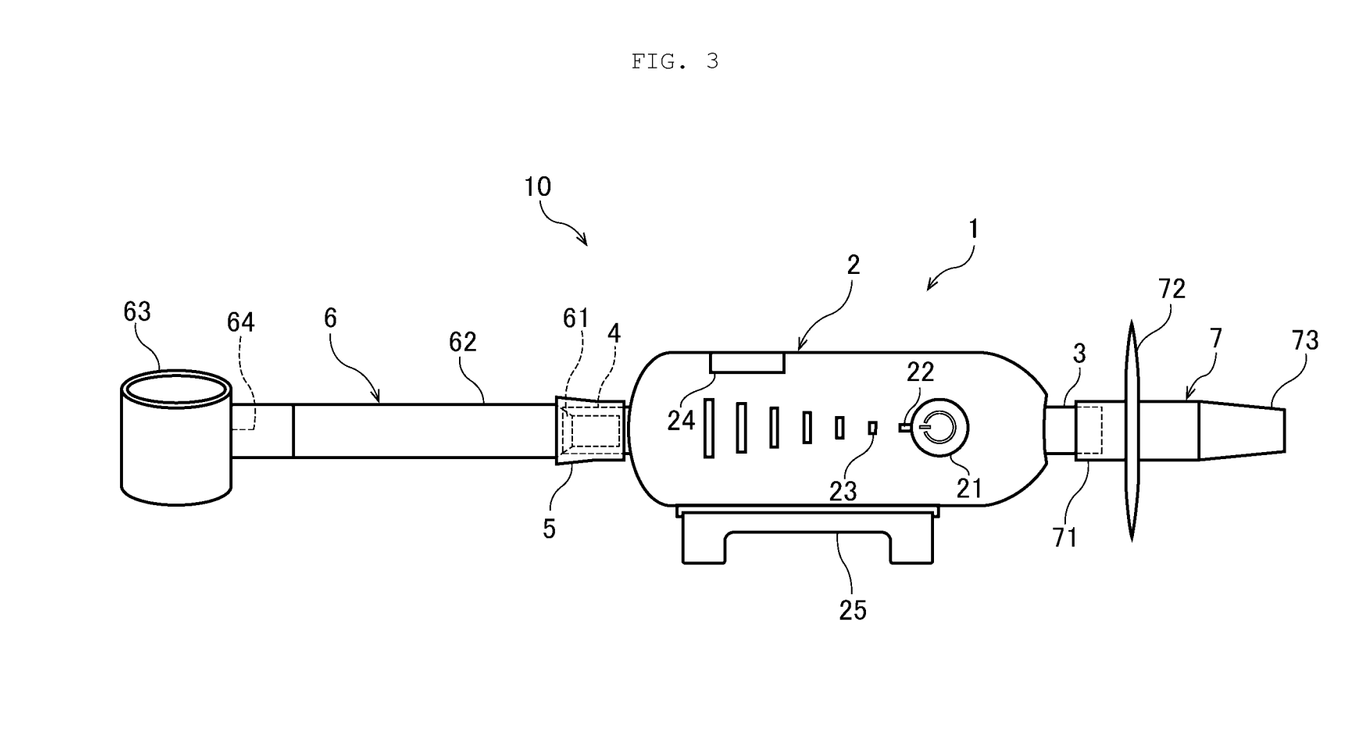
FIG. 3 is a plan view of an exhaled-air pressure measuring unit 10 provided with the exhaled-air pressure measuring device 1 of FIG. 1.

The thus-configured exhaled-air pressure measuring device 1 is utilized, for example, in the following manner. FIG. 3 is a plan view of an exhaled-air pressure measuring unit 10 provided with the exhaled-air pressure measuring device 1 of FIG. 1. The exhaled-air pressure measuring unit 10 is configured by the exhaled-air pressure measuring device 1 and the blowout 6 connected thereto. The blowout connection portion 4 of the exhaled-air pressure measuring device 1 is connected to the blowout 6 and covered with a blowing-mouth cover 5. The mouthpiece portion 3 has the mouthpiece 7 attached thereto.

The blowing-mouth cover 5, for example, having a cylinder shape, covers the mouthpiece body 61 of the blowout 6 described below. It covers the blowout connection portion 4 and the mouthpiece body 61 of the blowout 6, with the mouthpiece body 61 inserted in the blowout connection portion 4. The blowing-mouth cover 5 is formed of, for example, a semi-transparent flexible material (e.g., silicone).

The blowout 6 is utilizable for health promotion, medical treatment, cosmetic treatment and the like, and mainly includes the mouthpiece body 61, a pipe body 62, a stretchable body 63 and a wire body 64.

The mouthpiece body 61 is held by a user in the mouth such that air is exhaled by the user, has a cylinder shape and is formed of, for example, a plastic resin or the like. Since the blowout 6 itself is originally utilized such that a user exhales into it, the blowout 6 includes the mouthpiece body 61. However, in the embodiment, the blowout 6 is not singly utilized, and hence, the mouthpiece body 61 is not used so as to be held by a user in the mouth such that air is exhaled by the user. Hence, the mouthpiece body 61 is inserted into the blowout connection portion 4 and covered with the blowing-mouth cover 5, and then, is used for sending, to the blowout 6, air exhaled into the exhaled-air pressure measuring device 1 by a user.

The pipe body 62 is a pipe for sending air exhaled by a user to the stretchable body 63 after the exhaled air passes through the exhaled-air pressure measuring device 1. It extends in a cylinder shape from the mouthpiece body 61 and is formed of, for example, a plastic resin or the like. The pipe body 62 is inserted on the side opposite to the mouthpiece body 61 into one end of the stretchable body 63 and is connected by means of adhesive tape, an adhesive or the like to the stretchable body 63. The pipe body 62 has such an inner diameter and a length that a user can hold it easily and blow air easily from the mouthpiece body 61 into the stretchable body 63.

The stretchable body 63 is a member which is inflated with air exhaled by a user. It is a pouch-like portion having a tube shape and changeable in shape and is formed by paper having predetermined material qualities such as specified thickness, strength, density and durability. The stretchable body 63 has a substantially circle shape in cross section when inflated with air exhaled into the stretchable body 63, and it is curled into a spiral when air is not exhaled into it. The length of the stretchable body 63 (except the insertion part of the pipe body 62 into the stretchable body 63) is set in accordance with the purposes (what the blowout 6 is used for) such as health promotion, medical treatment and cosmetic treatment, the oral function condition of a user, or the like. Specifically, the length of the stretchable body 63 is set such that the quantity of exhaled air necessary for fully stretching out the stretchable body 63 equates with a suitable quantity of exhaled air preset for a usage purpose or the like.

The wire body 64 is a member which curls the stretchable body 63 into a spiral. It is a wire which has elasticity and is arranged straight along the longitudinal directions of the stretchable body 63 and which is, for example, formed of stainless-steel wire. The wire body 64 is curled into a spiral/coil when not given an external force (when air is not blown into the stretchable body 63), while it is straightened when given an external force (when air is blown into the stretchable body 63). If the wire body 64 is released after straightened by an external force, then the wire body 64 returns to the spiral shape by an elastic force of its own. The elastic force (elastic modulus) is set to a predetermined value such that the required exhaling force for stretching the stretchable body 63 becomes a suitable value (or an approximate value thereto) set in accordance with the usage purposes or the like, in other words, such that the stretchable body 63 will not be stretched if the force (exhaled air pressure) by which air is exhaled therein is not equal to or more than the predetermined value. In addition, the stretchable body 63 is designed such that if inflated with air exhaled by a user, then the exhaled air will come out at a fixed percentage thereof. Hence, if the exhaled air reaches a predetermined value or above, then the exhaled air will come out appropriately to maintain the required exhaling force.

The mouthpiece 7 is a member which covers the mouthpiece portion 3 so as to keep clean the exhaled-air pressure measuring device 1. It has a cylinder shape and is formed of a flexible material (e.g., silicone) subjected to antibacterial treatment. The mouthpiece 7 mainly includes a connection opening 71 to be connected to the mouthpiece portion 3, a disk-shaped guard 72 for preventing saliva or the like from adhering to the exhaled-air pressure measuring device 1, and a blowing mouth 73 for exhaling air. Into the cylinder of the mouthpiece 7, the front-end part of the mouthpiece portion 3 is inserted and pressed such that the mouthpiece 7 can be freely attached to and detached from it. The thus-formed mouthpiece 7 enables a user to hold it comfortably in the mouth and is capable of keeping the exhaled-air pressure measuring device 1 hygienic even if repeatedly utilized over a long period of time.

A user turns on the power by pressing the power switch 21, and thereby, the entire measuring device body 2 is supplied with electric power from the power source unit 28, so that the light of the power source LED 22 is turned on. Then, the user exhales air from the mouthpiece 7, and the exhaled air is sent through the mouthpiece portion 3 up to the measuring device body 2. At this time, the pressure sensor 26 measures the pressure of the exhaled air, and a detection signal is outputted to the microcomputer 27.

The microcomputer 27 compares the exhaled-air pressure of the detection signal with the stored thresholds and decides that it is equivalent to any of the level 0 to the level 7. Then, it turns on/off the lights of the exhaled-air-pressure level LEDs 23 which correspond to the exhaled-air pressure level obtained as the decision result. For example, as described above, let's assume that the blowout 6 set to the level 3 as the exhaled-air pressure level is connected and that a decision is made on the exhaled-air pressure level. If the exhaled-air pressure is 0 $cmH_2O$-12 $cmH_2O$ (the level 0), then the lights of all the exhaled-air-pressure level LEDs 23 are turned off. If the exhaled-air pressure is 12 $cmH_2O$-30 $cmH_2O$ (the level 1), then the light of the one exhaled-air-pressure level LED 23 on the right side is turned on. If the exhaled-air pressure is 30 $cmH_2O$-44 $cmH_2O$ (the level 2), then the lights of the two exhaled-air-pressure level LEDs 23 on the right side are turned on. If the exhaled-air pressure is 44 $cmH_2O$-80 $cmH_2O$ (the level 3), then the lights of the three exhaled-air-pressure level LEDs 23 on the right side are turned on. The microcomputer 27 is supposed to decide on the exhaled-air pressure level equal to, or more than, the level 4. However, the blowout 6 is designed so that the exhaled air comes out of it before the exhaled-air pressure reaches or exceeds the level 4. Hence, the microcomputer 27 will not make the decision if it is the level 4 or above. Therefore, the exhaled-air pressure level of the user can be objectively recognized.

In the exhaled-air pressure measuring device 1, the threshold of the exhaled-air pressure level can be changed in the following manner. A USB connector which has an external storage device connected thereto is connected to the USB terminal 24, and the external storage device operates to replace the threshold data stored in the microcomputer 27. Accordingly, in the exhaled-air pressure measuring device 1, a decision is made on the blowout 6, and the blowout 6 may be replaced with another blowout utilized for any different purpose. Therefore, another such blowout can be connected and utilized, and hence, a decision can be made on a blowout set to the exhaled-air pressure suitable for a usage purpose.

Figure 4:
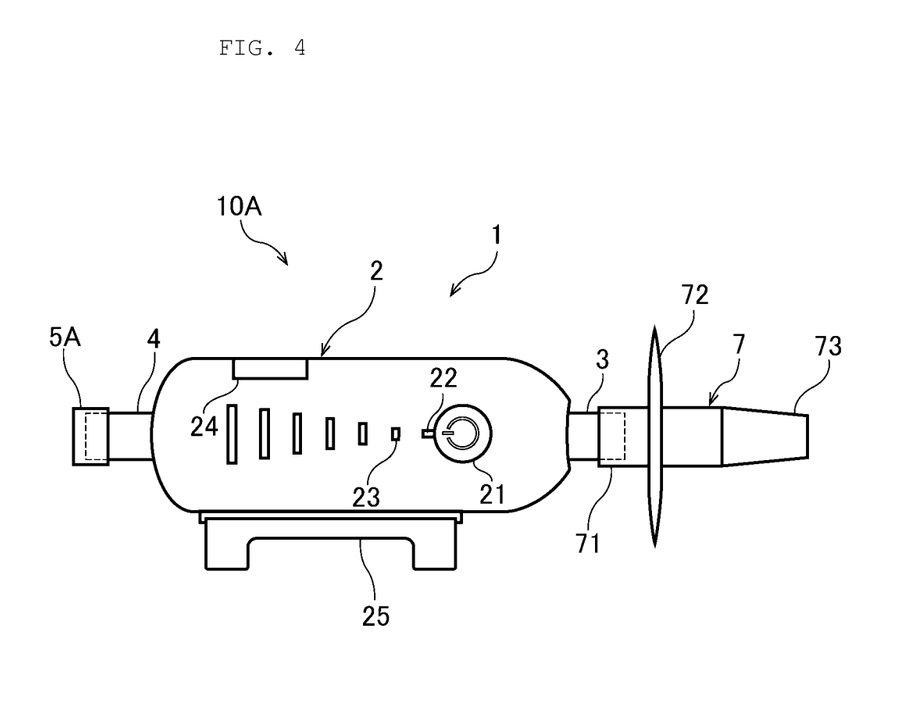
FIG. 4 is a plan view of an exhaled-air pressure measuring unit 10A provided with the exhaled-air pressure measuring device 1 of FIG. 1.

In addition, as described below, the exhaled-air pressure measuring device 1 can also be utilized without connecting the blowout 6 thereto. FIG. 4 is a plan view of an exhaled-air pressure measuring unit 10A provided with the exhaled-air pressure measuring device 1 of FIG. 1. The exhaled-air pressure measuring unit 10A is configured by the exhaled-air pressure measuring device 1 unprovided with the blowout 6. The blowout 6 is replaced with the attachment 5A, and in the respect that the blowout 6 is not provided, it differs from the exhaled-air pressure measuring unit 10. The attachment 5A is a cap-shaped member, one end of the member being open and the other end being closed, and is fitted onto the blowout connection portion 4 so as to cover it. The attachment 5A is formed of, for example, a semi-transparent flexible material (e.g., silicone). The attachment 5A is formed with an air hole (not shown), the air hole being located in a substantially central part in section thereof and having a predetermined size in the axial directions. As described above, the blowout 6 is designed such that the exhaled air comes out at a fixed percentage thereof. Instead of the blowout 6, the air hole is utilized so that the exhaled air comes out of the blowout connection portion 4. Except for the configuration and usage method described above, the exhaled-air pressure measuring unit 10A is the same as the exhaled-air pressure measuring unit 10.

In this case, similarly to the above, the microcomputer 27 compares the exhaled-air pressure of the detection signal with the stored thresholds and decides that it is equivalent to any of the level 0 to the level 7. Then, it turns on/off the lights of the exhaled-air-pressure level LEDs 23 which correspond to the exhaled-air pressure level obtained as the decision result. Specifically, If the exhaled-air pressure is 0 $cmH_2O$-12 $cmH_2O$ (the level 0), then the lights of all the exhaled-air-pressure level LEDs 23 are turned off. If the exhaled-air pressure is 12 $cmH_2O$-30 $cmH_2O$ (the level 1), then the light of the one exhaled-air-pressure level LED 23 on the right side is turned on. If the exhaled-air pressure is 30 $cmH_2O$-44 $cmH_2O$ (the level 2), then the lights of the two exhaled-air-pressure level LEDs 23 on the right side are turned on. If the exhaled-air pressure is 44 $cmH_2O$-80 $cmH_2O$ (the level 3), then the lights of the three exhaled-air-pressure level LEDs 23 on the right side are turned on. If the exhaled-air pressure is 80 $cmH_2O$-120 $cmH_2O$ (the level 4), then the lights of the four exhaled-air-pressure level LEDs 23 on the right side are turned on. If the exhaled-air pressure is 120 $cmH_2O$-150 $cmH_2O$ (the level 5), then the lights of the five exhaled-air-pressure level LEDs 23 on the right side are turned on. If the exhaled-air pressure is 150 $cmH_2O$ or above (the level 6), then the lights of all the exhaled-air-pressure level LEDs 23 are turned on. Therefore, the exhaled-air pressure level of the user can be objectively recognized.

In summary, in the exhaled-air pressure measuring device 1, the threshold data about the threshold for deciding on the exhaled-air pressure level are stored in the microcomputer 27. The threshold data is changeable by connecting an external storage device to the USB terminal 24 and allowing the external storage device to operate so as to replace the threshold data with other data. Therefore, the threshold for deciding on the exhaled-air pressure level can be easily set to an exhaled-air pressure level suitable for a usage purpose.

Although the embodiment of the present invention has been above described, the present invention is not limited to the embodiment as a specific configuration thereof. Without departing from the scope of the present invention, variations or the like in design should be included in the present invention. For example, in the embodiment, the threshold data are stored in the microcomputer 27 and is changeable by connecting an external storage device to the USB terminal 24 and allowing the external storage device to operate so as to replace the threshold data with other data. However, the measuring device body 2 may be configured such that the threshold data are not stored therein. In such a case, an external medium such as a USB memory which has the threshold data in storage is connected to the USB terminal 24, so that the threshold data will be available. This makes it possible to form the microcomputer 27 by low-cost component parts.

In addition, the measuring device body 2 may have several pieces of the threshold data stored therein, or an external storage device may have several pieces of the threshold data stored therein. In such a case, the several pieces of threshold data will be changeable by means of a switch or the like. Therefore, the threshold for deciding on the exhaled-air pressure level can be more easily set to an exhaled-air pressure level suitable for a usage purpose.

DESCRIPTION OF THE SYMBOLS

1 exhaled-air pressure measuring device
2 measuring device body
3 mouthpiece portion
4 blowout connection portion
5 blowing-mouth cover
6 blowout
7 mouthpiece
21 power switch
22 power source LED
23 exhaled-air-pressure level LED (indication section)
24 USB terminal
25 blowout holder
26 pressure sensor
27 microcomputer (deciding section)
28 power source unit
29 external connection terminal
61 mouthpiece body
62 pipe body
63 stretchable body
64 wire body

The invention claimed is:

1. An exhaled-air pressure measuring device, comprising:
   a blowout connection portion;
   a mouthpiece portion configured to be held by a user in the mouth such that air is exhaled by the user, wherein the mouthpiece portion is in fluid communication with the blowout connection portion;
   an indication section; and
   a measuring device body which measures the pressure of the exhaled air into the mouthpiece portion by the user, and on the basis of a result of the measurement, decides on an exhaled-air pressure level which corresponds to the pressure of the exhaled air, wherein the measuring device body comprises:
      a storage section for storing threshold data representing predetermined thresholds of a plurality of the exhaled-air pressure levels, the predetermined thresholds corresponding to a plurality of types of blowouts suitable for different usage purposes;
      a deciding section for deciding on the exhaled-air pressure level from the result of the measurement on the basis of the predetermined thresholds; and
      a terminal connected to an external storage device so that the external storage device accesses the storage section,
   wherein the external storage device is configured to replace the threshold data with other threshold data upon connection via the terminal, wherein the indication section is configured to provide a level indicator for indicating whether a blowout connected to the blowout connection portion is suitable for a usage purpose based on the exhaled air pressure level of the user exceeding one of the predetermined thresholds.

2. The exhaled-air pressure measuring device according to claim 1, wherein the indication indicates an exhaled-air pressure level.

3. The exhaled-air pressure measuring device according to claim 1, wherein an attachment or a blowout is optionally attached to the blowout connection portion of the measuring device body, the attachment being formed with an air hole having a predetermined size for releasing the exhaled air into the mouthpiece portion, and the blowout including a stretchable body having a tube shape and changeable in shape, the stretchable body being stretched when air is exhaled into the blowout from the mouthpiece portion and being curled into a spiral when air is not exhaled into the blowout from the mouthpiece portion.

* * * * *